United States Patent
Babcook et al.

(10) Patent No.: US 7,754,433 B2
(45) Date of Patent: Jul. 13, 2010

(54) IDENTIFICATION OF HIGH AFFINITY MOLECULES BY LIMITED DILUTION SCREENING

(75) Inventors: John Babcook, Vancouver (CA); Xiao-Chi Jia, San Mateo, CA (US); Jaspal Singh Kang, Surrey (CA); Li Zhang, Fremont, CA (US)

(73) Assignee: Amgen Fremont Inc., Fremont, CA (US)

( * ) Notice: Subject to any disclaimer, the term of this patent is extended or adjusted under 35 U.S.C. 154(b) by 694 days.

(21) Appl. No.: 10/309,421

(22) Filed: Dec. 2, 2002

(65) Prior Publication Data

US 2003/0186327 A1    Oct. 2, 2003

Related U.S. Application Data

(60) Provisional application No. 60/337,250, filed on Dec. 3, 2001.

(51) Int. Cl.
*G01N 33/53* (2006.01)
(52) U.S. Cl. .............................. 435/7.1; 435/6; 435/7.2
(58) Field of Classification Search .................. 435/7.1, 435/7.2, 7.24, 7.9, 7.92, 7.91
See application file for complete search history.

(56) References Cited

U.S. PATENT DOCUMENTS

| | | | |
|---|---|---|---|
| 5,324,633 A | | 6/1994 | Fodor et al. |
| 5,426,029 A | * | 6/1995 | Rittershaus et al. ........ 435/7.21 |
| 5,434,076 A | | 7/1995 | Freedman et al. |
| 5,514,554 A | | 5/1996 | Bacus |
| 5,541,070 A | | 7/1996 | Kauvar |
| 5,585,241 A | | 12/1996 | Lindmo et al. |
| 5,800,815 A | | 9/1998 | Chestnut et al. |
| 5,834,597 A | | 11/1998 | Tso et al. |
| 5,929,212 A | | 7/1999 | Jolliffe et al. |
| 5,939,326 A | | 8/1999 | Chupp et al. |
| 6,187,310 B1 | | 2/2001 | Mann et al. |
| 6,207,160 B1 | | 3/2001 | Victoria et al. |
| 6,455,244 B1 | * | 9/2002 | Guichard et al. ................ 435/5 |
| 2002/0086441 A1 | | 7/2002 | Baranov et al. |
| 2002/0155422 A1 | | 10/2002 | Ingber et al. |
| 2003/0118985 A1 | | 6/2003 | Hunt et al. |
| 2004/0059519 A1 | | 3/2004 | Chandler et al. |

FOREIGN PATENT DOCUMENTS

| | | |
|---|---|---|
| WO | WO 93/03770 | 3/1993 |
| WO | WO 03/048729 A | 6/2003 |
| WO | WO 03/048730 A3 | 6/2003 |

OTHER PUBLICATIONS

Harlow Antibody Laboratory Manual, 1988 Cold Spring Harbor, p. 141-155.*

Batra et al. Recombinant Anti-ErbB2 Immunotoxins Containing *Psueudomonas Exotoxin*, Proc. Natl. Acad. Sci. USA, Jul. 1992, vol. 89, pp. 5867-5871.

Watkins et al. "Determination of the relative affinities of antibody fragments expressed in *Escherichia coli* by enzyme-linked immunosorbent assay." *Analytical Biochemistry*. 253(1):37-45 (1997).

Clynes et al. "Inhibitory Fc receptors modulate in vivo cytoxicity against tumor targets." *Nature Medicine*. 6(4):443-446 (2000).

Eisen et al. "Cluster analysis and display of genome-wide expression patterns." *Proc. Natl. Acad. Sci. USA*. 95:14863-14868 (1998).

Jia et al. "A novel method of multiplexed competitive antibody binning for the characterization of monoclonal antibodies." *Journal of Immunological Methods*. 288:91-98 (2004).

Kuroki et al. "A simple solid-phase competition assay with labeled antigen." *Methods in Molecular Biology*. 66:47-53.

O'Hare et al. "A simple method for determining $K_A$s as of both low and high affinity IgG antibodies." *Journal of Immunological Methods*. 218:161-167 (1998).

Perton et al. "Comparison of three methods for competitive binding of monoclonal antibodies- The localization of antigenic sites for monoclonal antibodies on *Panulirus interruptus* hemocyanin" *Journal of Immunological Methods*. 190(1):117-125 (1996).

Kuroki et al. "Determination of epitope 1-52 specificities of a large number of monoclonal antibodies by solid-phase mutual inhibition assays using biotinylated antigen." *Immunological Investigations*. 21(6):523-538 (1992).

Vignali, D.A.A. "Multiplexed particle-based flow cytometric assays." *Journal of Immunological Methods*. 243(1-2):243-255 (2000).

Lindmo et al. "Immunometric assay by flow cytometry using mixtures of two particle types of different affinity." *Journal of Immunological Methods*. 126:183-189 (1990).

Lange et al. "Epitope mapping of homologous and cross-reactive antigens by monoclonal antibodies to streptococcal cell membrane (mAb to SCM)." *Molecular Immunology*. 33(9):777-786 (1996).

Tarassishin et al. "A competitive avidin-biotin ECL dot-blot assay for epitope mapping of monoclonal antibodies." *Journal of Virological Methods*. 49(1):90-92 (1994).

Park et al. "A latex bead-based flow cytometric immunoassay capable of simultaneous typing of multiple pneumococcal serotypes (multibead assay)." *Clinical and Diagnostic Laboratory Immunology*. 7(3):486-488 (2000).

Eren et al. *Hepatology*. 32:588-596 (2000).

(Continued)

*Primary Examiner*—Jacob Cheu
(74) *Attorney, Agent, or Firm*—Knobbe Martens Olson & Bear LLP

(57) ABSTRACT

Methods are disclosed for determining the relative binding affinities of molecules for their binding partner. One type of molecule is an antibody, which has an antigen binding partner. Antibodies are tested for binding against limited dilutions of antigen. Antibodies that bind to the most dilute antigen concentrations are determined to have a higher relative binding affinity for the antigen than antibodies that only bind to more concentrated antigen preparations.

20 Claims, No Drawings

OTHER PUBLICATIONS

Watkins, J.D. et al. "Determination of the relative affinities of antibody fragments expressed in *Escherichia coli* by enzyme-linked immunosorbent assay." Analytical Biochemistry, Nov. 1, 1997, vol. 253, No. 1, pp. 37-45.

Crowther, John R., "ELISA Theory and Practice," *Methods in Molecular Biology*, vol. 42, Humana Press, Inc., New Jersey (1995).

European Patent Office Notice of Opposition, Application No. 02792319.2—1223 / 1554576, Reference AGB-101-EP (Jun. 10, 2008).

Pollock et al., "Identification of mutant monoclonal antibodies with increased antigen binding," *Proc. Natl. Acad. Sci. USA*, vol. 85, Immunology, pp. 2298-2302 (Apr. 1988).

Pope et al., "In vitro selection of a high affinity antibody to oestradiol using a phage display human antibody library," *Immunotechnology* 2, pp. 209-217 (1996).

Wu et al., "Stepwise in vitro affinity maturation of Vitaxin, an $\alpha_v\beta_3$-specific humanized mAb," *Proc. Natl. Acad. Sci. USA*, vol. 95, Biochemistry, pp. 6037-6042 (May 1998).

* cited by examiner

IDENTIFICATION OF HIGH AFFINITY MOLECULES BY LIMITED DILUTION SCREENING

RELATED APPLICATIONS

This application claims priority to related U.S. Provisional Application No. 60/337,250 filed Dec. 3, 2001.

FIELD OF THE INVENTION

Embodiments of the invention relate to techniques for determining the binding affinities of molecules for a molecule binding partner. More specifically, embodiments of the invention relate to methods of determining the relative binding affinity of antibodies to a target antigen by contacting each antibody with limited dilutions of antigen.

BACKGROUND OF THE INVENTION

During an immune response B-cells are stimulated to generate antibodies that specifically bind molecules that activate the immune system. The genetic recombination events involved with the synthesis of antibodies enables animals to create an immense diversity of antibodies each with its own characteristics such as binding specificity and binding affinity. Antibodies are currently being used for diverse diagnostic, imaging, or therapeutic applications. Antibodies that can be successfully used for diagnostic, imaging or therapeutic applications often require special characteristics. In particular, the kinetic properties of the antibody often dictate their utility. In general, the effectiveness or suitability of an antibody shows a strong positive correlation with the antibody's affinity for its target. As higher affinity antibodies are able to bind their target faster and remain bound to the target longer, they generally are effective at lower concentrations. Monoclonal antibodies (mAbs) can be generated by a variety of techniques including hybridoma technology, which involves fusing antibody-producing B-cells with cancerous myeloma cells. (Kohler & Milstein (1975) *Nature* 256: 52-53). The resulting hybridoma cell is an "immortalized" cell that secretes an antibody of single specificity (monoclonal antibody). An alternative method for monoclonal antibody generation is termed the Selected Lymphocyte Antibody Method (SLAM), described in U.S. Pat. No. 5,627,052 entitled "Methods for the production of proteins with a desired function" and in "A novel strategy for generating monoclonal antibodies from single, isolated lymphocytes producing antibodies of defined specificities" Babcook et al. (1996) *Proc Natl Acad Sci USA*. 93:7843-8. This method allows one to first identify B-cells that are making antibodies with desired characteristics such as binding specificity, function, and optimal kinetics. The selected B-cells are then isolated and the antibody variable domain genes encoding the binding portion of the antibody are rescued by molecular techniques, such as the polymerase chain reaction (PCR), and cloned into expression vectors having an antibody constant region domain. The expression vectors are then transfected into cells, such as CHO or NSO cells, to produce secreted antibody molecules. This process allows the virtually unlimited production of the desired antibody. Other methodologies such as phage display or the viral immortalization (including EBV) of B-cells have also been used successfully in the generation of monoclonal antibodies.

During the SLAM process, millions of B-cells are screened for the specificity, function and kinetic characteristics of the antibodies they produce. For a selected target, thousands of target-specific B-cells might be identified. Examples of known methods of screening include screening for antibodies which (1) bind to natively expressed antigen on the cell surface, (2) bind cell lines and induce apoptosis, (3) bind cells and either induce proliferation or block proliferation, and (4) bind to ligand and block binding of the ligand to receptor and vice versa. To determine formal affinity measurements of large panels of antibodies is a time-consuming, expensive, and inefficient process for identifying optimal antibodies. Accordingly, what is needed is a simple, rapid, and accurate mechanism for screening antibodies to determine their relative binding characteristics.

SUMMARY OF THE INVENTION

The present invention includes a method for kinetically ranking each antibody in an antibody set by preparing a set of diluted antigen preparations and thereafter measuring the binding of each antibody in the set of antibodies to the diluted antigen preparations. During the binding assay, antibody and antigen are combined, the binding reaction is allowed to go to equilibrium, and after equilibrium is achieved, each antibody is preferably labeled with a detectable label, and the strength each antibodies label signal is related to the binding affinity of the antibody for a diluted antigen preparation. A comparison of each antibody's relative affinity for each particular antigen preparation can thereby be performed. Antibodies that bind to the more dilute antigen preparations have a higher relative affinity for the antigen, whereas antibodies that only bind to more concentrated antigen preparations have a relatively lower binding affinity to the antigen.

One embodiment of the invention is a method of determining the relative binding affinities of antibodies to an antigen. This embodiment includes: determining the limiting concentration of an antigen that maximizes the detectable range of antibody affinities for said antigen; providing a set of antibody solutions, wherein the concentration of antibodies in each antibody solution is known; incubating the limiting concentration of antigen with each member of the set of antibody solutions; measuring the relative degree to which the antibodies in each member of the set of antibody solutions binds to the limiting concentration of antigen; and ranking the antibodies in each member of said set of antibody solutions based on their binding affinity to said different dilutions in order to determine the relative binding affinities of each of said different antibodies to said antigen.

Another embodiment of the invention is a method of determining the relative binding affinities of a set of antibodies to an antigen which includes: providing an antigen solution comprising a first dilution of the antigen, wherein said antigen is labeled with a first label, and a second dilution of the antigen, wherein said antigen is labeled with a second label; providing a set of antibody solutions wherein each antibody solution has substantially the same relative concentration of said antibody; measuring the binding of the antibody to the first dilution of said antigen; measuring the binding of the antibody to the second dilution of the antigen; and ranking the antibody in the set of antibody solutions which bind to a relatively more dilute antigen preparation as having a higher relative affinity and the antibody that substantially only bind to relatively more concentrated antigen preparations as having a relatively lower binding affinity to the antigen.

Still another embodiment is a method of determining the relative binding affinities of a set of molecules to a molecule binding partner. This method includes: determining the limiting concentration of a molecule binding partner that maximizes the detectable range of molecule affinities for said molecule binding partner; providing a set of molecule solutions, wherein the concentration of molecules in each molecule solution is known; incubating the limiting concentration of molecule binding partners with each member of the set of molecule solutions; measuring the relative degree to which the molecules in each member of the set of molecule solutions binds to the limiting concentration of molecule binding partners; and ranking the molecules in each member of said set of molecule solutions based on their binding affinity to said different dilutions in order to determine the relative binding affinities of each of said different molecules to said molecule binding partners.

DETAILED DESCRIPTION

Embodiments of the invention relate to methods for rapidly determining the differential binding properties within a set of antibodies. Accordingly, rapid identification of optimal antibodies for binding to a target can be determined. Any set of antibodies raised against a particular target antigen may bind to a variety of epitopes on the antigen. In addition, antibodies might bind to one particular epitope with varying affinities. Embodiments of the invention provide methods for determining how strongly or weakly an antibody binds to a particular epitope in relation to other antibodies generated against the antigen.

One embodiment of the invention is provided by preparing a set of diluted antigen preparations and thereafter measuring the binding of each antibody in a set of antibodies to the diluted antigen preparations. A comparison of each antibody's relative affinity for a particular concentration of antigen can thereby be performed. Accordingly, this method discerns which antibodies bind to the more dilute concentration of antigen, or to the more concentrated antigen preparations, as part of a comparative assay for the relative affinity of each antibody in a set.

Another embodiment of the invention is provided by preparing a set of diluted antibody preparations and thereafter measuring the binding of an antigen to each of the diluted antibody preparations. A comparison of each antibody's relative affinity for a particular antigen can thereby be performed. Accordingly, this method discerns whether a particular concentration of an antigen binds to the more dilute concentration of antibody preparations, or to the more concentrated antibody preparations, as part of a comparative assay for the relative affinity of each antibody in a set.

Although a process is disclosed in which an antibody's relative affinity can be determined, a similar protocol can be foreseen for the identification of high affinity antibody fragments, protein ligands, small molecules or any other molecule with affinity toward another. Thus, the invention is not limited to only analyzing binding of antibodies to antigens.

One embodiment of the invention provides a method for analyzing the kinetic properties of antibodies to allow ranking and selection of antibodies with desired kinetic properties. Affinity, as defined herein, reflects the relationship between the rate at which one molecule binds to another molecule (association constant, $K_{on}$) and the rate at which dissociation of the complex occurs (dissociation constant, $K_{off}$). When an antibody and target are combined under suitable conditions, the antibody will associate with the target antigen. At some point the ratio of the amount of antibody binding and releasing from its target reaches an equilibrium. This equilibrium is referred to as the "affinity constant" or just "affinity".

When binding reactions having identical concentrations of antibody and target molecule are compared, reactions containing higher affinity antibodies will have more antibodies bound to the target at equilibrium than reactions containing antibodies of lower affinity.

In assays where the binding of one molecule to another is measured by the formation of complexes which generate a signal, the amount of signal is proportional to the concentrations of the molecules as well as to the affinity of the interaction. For purposes of the present disclosure, assays are employed to measure formation of complexes between antibodies and their targets (on antigens), where signals being measured in such assays may be proportional to the concentrations of antibody or antibodies, concentration of target antigen, and the affinity of the interaction. Suitable assay methods for measuring formation of antibody-target complexes include enzyme linked immunosorbent assays (ELISA), fluorescence-linked immunosorbent assays (including Luminex systems, FMAT and FACS sytems), radioisotopic assay (RIA) as well as others which can be chosen by one of skill in the art.

Another aspect of the present invention includes methods for kinetically ranking antibodies by affinity based on the signal strength of an assay such as an assay listed above, when the target or antigen is provided at limiting concentrations. Antibody and antigen are combined, the binding reaction is allowed to go to equilibrium, and after equilibrium is achieved, an assay is performed to determine the amount of antibody bound to the target or antigen. According to one aspect of the present invention, the amount of bound antibody detected by the assay is directly proportional to the affinity of the antibody for the target or antigen. At very low concentrations of antigen, some antibodies of low affinity will not generate a detectable signal due to an insufficient amount of bound antibody. At the same very concentrations of antigen, antibodies of moderate affinity will generate low signals, and antibodies with high affinity will generate strong signals.

During a standard assay using moderate to high concentrations of target, a collection of different antibodies having different affinities for the same target antigen may generate signals of equal or similar intensity. However, as the amount of antigen is diluted, it becomes possible to discern differences in affinity among the antibodies. Using limiting concentrations of target antigen in the assay in accordance with the teachings of the present disclosure, it is possible to establish a kinetic ranking of a collection of antibodies against the same target antigen.

Under conditions of limiting amounts of antigen, a collection of antibodies against the same antigen will give a range of signals from high to low or no signal, even though in the original assay using high to moderate levels of antigen, some of these antibodies may have produced signals of similar apparent strength. Antibodies can thus be affinity-ranked by their signal intensity in a limiting antigen assay carried out in accordance with the teachings of the present disclosure.

Another aspect of the invention is a method of determining antibodies with higher affinities than currently known and characterized antibodies. This method involves using the characterized antibodies as kinetic standards. A plurality of test antibodies are then measured against the kinetic standard antibodies to determine those antibodies that bind to more dilute antigen preparations than to the standard antibodies. A plurality of test antibodies is then measured against the kinetic standard antibody to determine those antibodies which have more antibody bound to a given dilute preparation of antigen. This allows the rapid discovery of antibodies that have a higher affinity for antigen in comparison to the kinetic standard antibodies.

In one preferred embodiment, an ELISA is used in a limiting antigen assay in accordance with the present disclosure.

It has been empirically determined that supernatants of cultured B-cells generally secrete antibodies in a concentration range from 20 ng/ml to 800 ng/ml. Because there is often a limited amount of supernatant from these cultures, B-cell culture supernatants are typically diluted 10-fold for most assays, giving a working concentration of from 2 ng/ml-80 ng/ml for use in affinity determination assays. In one aspect of the invention, the appropriate concentration of target antigen used to coat ELISA plates was determined by using a reference solution from a monoclonal antibody at a concentration of 100 ng/ml. This number could change depending on the concentration range of test antibodies and the affinity of the reference antibody, such that the concentration of target antigen required to give half-maximal signal in a ELISA-based measurement of antibody/antigen binding can be empirically determined. This determination is discussed in more detail below.

Antigen at an empirically determined optimal coating concentration was used in affinity measurement assays to discern the antibodies produced by various B-cell cultures that gave an ELISA value higher than a reference monoclonal antibody. According to the methods of the present invention, the only way to obtain a higher signal than that obtained using the reference antibody is if (1) the antibody is of higher affinity than the reference antibody or (2) the antibody has the same affinity but is present in a higher concentration that the reference monoclonal antibody. As disclosed previously, antibodies in B-cell culture supernatants are usually at concentrations of between 20-800 ng/ml and are diluted to a working concentration of between 2 to 80 ng/ml. In one embodiment, test antibodies at a concentration of between 2 to 80 ng/ml are used in assays having a reference antibody concentration of 100 ng/ml. The signal achieved from the test antibodies is compared to that of the 100 ng/ml reference antibody. If antibodies within the test group are found to have a higher signal, then the antibody is assumed to be of a higher affinity than the reference antibody.

In another embodiment, antibodies generated from hybridomas were ranked using a limiting kinetic antigen assay in an ELISA-based protocol. The binding affinities for these antibodies was confirmed by quantifying and kinetically ranked the antibodies using a Biacore system. As is known, the Biacore system gives formal kinetic values for the binding coefficient between each antibody and the antigen. It was determined that the kinetic ranking of antibodies using the limiting antigen assay as taught by the present disclosure closely correlated with the formal kinetic values for these antibodies as determined by the Biacore method, as shown in Table 5 (Example 5).

Briefly, the Biacore technology uses surface plasmon resonance (SPR) to measure the decay of antibody from antigen at various concentrations of antigen and at a known concentration of antibody. For example, chips are loaded with antibody, washed, and the chip is exposed to a solution of antigen to load the antibodies with antigen. The chip is then continually washed with a solution without antigen. An initial increase in SPR is seen as the antibody and antigen complex forms, followed by decay as the antigen-antibody complex dissociates. This decay in signal is directly proportional to antibody affinity. Similarly this method could run the reverse assay with limited concentrations of antibody coated on the chip.

Using the Luminex (MiraiBio, Inc., Alameda, Calif.) technology antibodies are assayed for how they bound a plurality of different antigen coated beads. In this assay each bead set is preferably coated with a different concentration of antigen. As the Luminex reader has the ability to multiplex all the beads sets, the bead sets are combined and antibody binding to each of the different bead sets are determined. The behavior of antibodies on the differentially coated beads can then be tracked. Once normalized for antibody concentration, then antibodies which maintain a high degree of binding as one moves from non-antigen limiting concentrations to limited antigen concentrations correlate well to high affinity. Advantageously, these differential shifts can be used to relatively rank antibody affinities. For example, samples with smaller shifts correspond to higher affinity antibodies and antibodies with larger shifts correspond to lower affinity antibodies.

TABLE 1

Comparison of Affinity Rankings Between Biacore and Luminex Methods

BiaCore Affinity Measurements

| $k_a\ (M^{-1}s^{-1})$ | $k_d\ (s^{-1})$ | Biacore Med-res $K_D\ (nM)$ | Rank | Luminex rank |
|---|---|---|---|---|
| $9.9 \times 10^5$ | $9.3 \times 10^{-3}$ | 9.4 | 1 | 1 |
| $2.7 \times 10^5$ | $4.2 \times 10^{-3}$ | 16 | 2 | 14 |
| $3.1 \times 10^5$ | $5.6 \times 10^{-3}$ | 18 | 3 | 57 |
| $8.2 \times 10^5$ | $2.7 \times 10^{-2}$ | 33 | 4 | 83 |
| $1.4 \times 10^6$ | $6.2 \times 10^{-2}$ | 42 | 5 | 116 |
| $2.9 \times 10^5$ | $1.6 \times 10^{-2}$ | 54 | 6 | 123 |

In another embodiment of the invention, a series of limited concentrations of the antibody being tested are compared to a standard solution of antibody. Such a method using limiting concentrations of antibody would appear to be a "reverse" of the method using limiting antigen concentrations, but it provides a similar mechanism for rapidly screening a set of antibodies to determine each antibody's relative affinity for the target antigen. Other plates that are, or can be, chemically modified to allow covalent or passive coating can also be used. One of skill in the relevant art can devise further modifications of the methods presented herein to carry out an assay using limiting antibody dilution to screen and kinetically rank test antibodies.

Determining Optimal Bound Antigen Concentration

Embodiments of the limiting antigen assay method are practiced using a method by which antigen is bound or attached to a stationary surface prior to subsequent manipulations. The surface is preferably part of a vessel in which subsequent manipulations may occur; more preferably, the surface is in a flask or test tube, even more preferably the surface is in the well of a microtiter plate such as a 96-well plate, a 384-well plate, or a 864-well plate. Alternately, the surface to which antigen is bound may be part of a surface such as a slide or bead, where the surface with bound antigen may be manipulated in subsequent antibody binding and detection steps. Preferably, the process by which the antigen is bound or attached to the surface does not interfere with the ability of antibodies to recognize and bind to the target antigen.

In one embodiment, the surface is coated with streptavidin and the antigen is biotinylated. In a particularly preferred embodiment, the plate is a microtiter plate, preferably a 96-well plate, having streptavidin coating at least one surface in each well, and the antigen is biotinylated. Most preferably, the plate is Sigma SA 96-well plate and the antigen is biotinylated with Pierce EZ-link Sulpho-NHS Biotin (Sigma-Aldrich Canada, Oakville Ontario, CANADA). Alternative methods of biotinylation which attach the biotin molecule to other moieties can also be used.

In the unlikely event that an antigen cannot be biotinylated, alternative surfaces to which antigen can be bound can be substituted. For example, the Costar® Universal-BIND™ surface, which is intended to covalently immobilize biomolecules via an abstractable hydrogen using UV illumination resulting in a carbon-carbon bond. (Corning Life Sciences, Corning, N.Y.). Plates, for example, Costar® Universal-BIND™ 96-well plates, may be used. One of skill in the art can modify subsequent manipulations in the event that the use of alternate surfaces such as Costar® Universal-BIND™ increases the time of the assay and/or requires the use of more antigen.

In one embodiment of the present invention, a "checkerboard" assay design is used to find optimal concentration of bound antigen. One example is shown below in Table 2. The following description includes a disclosure of the steps to determine the optimal coating concentration of biotinylated antigen using 96-well plates coated with streptavidin. This disclosure is intended merely to illustrate one way to practice various aspects of the present invention. The scope of the present invention is not limited to the methods of the assay described above and below, as one of skill in the art can practice the methods of the present invention using a wide variety of materials and manipulations. Methods including but not limited to; expression of antigen on cells (transient or stable), using phage which express different copy number of antigen per phage.

Antigen Dilution and Distribution.

An antigen to be tested is selected. Such an antigen may be, for example, any antigen that might provide a therapeutic target by antibodies. For example, tumor markers, cell surface molecules, Lymphokines, chemokines, pathogen associated proteins, and immunomodulators are non-limiting examples of such antigens.

A solution of antigen at an initial concentration, preferably about 1 ug/ml, is diluted in a series of stepwise dilutions. Diluted samples are then placed on surfaces such as in the wells of a microtiter plate, and replicates of each sample are also distributed on surfaces. Antigen solutions may contain blocking agents if desired. In a preferred embodiment, serial dilutions of antigen are distributed across the columns of a 96-well plate. Specifically, a different antigen dilution is placed in each column, with replicate samples in each row of the column. In a 96-well plate, replicates of each dilution are placed in rows A-H under each column. Although the standard dilutions vary from antigen to antigen, the typical dilution series starts at 1 ug/ml and is serially diluted 1:2 to a final concentration of about 900 pg/ml.

In one embodiment, biotinylated antigen is diluted from a concentration of 1 ug/ml to 900 pg/ml horizontally across a 96 well plate. While a preferred blocking buffer is a PBS/Milk solution, others buffers such as BSA diluted in PBS can be substituted. In another embodiment, biotinylated antigen is diluted from a concentration of 1 ug/ml to 900 pg/ml in 1% skim milk/1× PBS pH 7.4, and pipetted into the wells of columns 1 to 11 of a Sigma SA (streptavidin) microtiter plate, with 8 replicates of each dilution placed in rows A-H of each column. Column 12 is left blank, serving as the "antibody-only" control. The final volume in each well is 50 ul. Antigen is incubated on the surface (e.g., in the wells of the plate) for a suitable amount of time for the antigen to become attached to the surface; incubation time, temperature, and other conditions can be determined from manufacturer's instructions and/or standard protocols for the surface being used. After incubation, excess antigen solution is removed. If needed, plates are then blocked with a suitable blocking solution containing, e.g., skim milk, powdered milk, BSA, gelatin, detergent, or other suitable blocking agents, to prevent non-specific binding during subsequent steps.

Plates with biotinylated antigen are then incubated for a suitable amount of time for antigen to bind or attach to the surface. Biotinylated antigen in a Sigma SA plate is incubated at room temperature for 30 minutes. Excess biotinylated antigen solution is then removed from the plate. In this embodiment, blocking is not necessary because Sigma SA plates are pre-blocked.

In another embodiment using Costar® Universal-BIND™ plates, antigen is passively adsorbed overnight at 4 degrees C. in 1× PBS pH 7.4, 0.05% azide. Generally, if Costar® Universal-BIND™ plates are used, the initial concentration of antigen is a somewhat higher concentration, preferably 2-4 ug/ml. The next morning, excess antigen solution is removed from Costar® Universal-BIND™ plate or plates, preferably by "flicking", and each plate is exposed to UV light at 365 nm for four (4) minutes. Each plate is then blocked with 1% skim milk/1× PBS pH 7.4 at 100 ul of blocking solution per well, for 30 minutes.

After incubation with antigen and removal of excess antigen solution, and blocking, if necessary, plates are washed four times (4×) with tap water. Plates may be washed by hand, or a microplate washer or other suitable washing tool may be used.

Reference Antibody Dilution and Distribution.

A reference antibody that recognizes and binds to the antigen is then added. The reference antibody is preferably a monoclonal antibody, but can alternatively be polyclonal antibodies, natural ligands or soluble receptors, antibody fragments or small molecules.

A solution of reference antibody, also known as anti-antigen antibody, at an initial concentration, preferably about 1 ug/ml, is diluted in a series of stepwise dilutions. Diluted samples are placed on surfaces such as in the wells of a microtiter plate, and replicates of each sample are also distributed on surfaces. Serial dilutions of reference antibody are distributed across the rows of a 96-well plate. Specifically, each reference antibody dilution is placed in a row, with replicate samples placed in each column of the row. In a 96-well plate, a different dilution of reference antibody is placed in each row, with replicates of each dilution placed in each column across each row starting at an initial concentration of about 1 ug/ml progressively and diluted 1:2 seven times for a series of seven wells. An ending concentration of about 30 ng/ml is used as the standard solution series. Solutions of reference antibody are incubated with bound antigen under suitable conditions determined by the materials and reagents being used, preferably about 24 hours at room temperature. One of skill in the art can determine whether incubation for longer or shorter times, or at higher or lower temperatures would be suitable for a particular embodiment.

Optional Step: Incubation with Shaking. If desired, the plate may be tightly wrapped and incubation of the reference antibody with bound antigen may be carried out with shaking to promote mixing and more efficient binding. Plates containing reference antibody and bound antigen may be incubated overnight with shaking, for example as provided by a Lab Line Microplate Shaker at setting 3.

Add Detection Antibody.

Plates are washed to remove unbound reference antibody, preferably about five times (5x) with water. Next, a labeled detection antibody that recognizes and binds to the reference antibody is added, and the solution is incubated to permit binding of the detection antibody to the reference antibody. The detection antibody may be polyclonal or monoclonal. The detection antibody may be labeled in any manner that allows detection of antibody bound to the reference antibody. The label may be an enzymatic label such as alkaline phosphatase or horseradish peroxidase (HRP), or a non-enzymatic label such as biotin or digoxygenin, or may be a radioactive label such as $^{32}P$, $^{3}H$, or $^{14}C$, or may be any other label suitable for the assay based on reagents, materials, and detection methods available.

Following labeling, 50 ul of goat anti-Human IgG Fc HRP polyclonal antibody (Pierce Chemical Co, Rockford Ill., catalog number 31416) at a concentration of 0.5 ug/ml in 1% skim milk, 1x PBS pH 7.4 is added to each well of a microtiter plate. The plate is then incubated for 1 hr at room temperature.

Excess solution containing detection antibody is removed, and plates are washed with water repeatedly, preferably at least five times, in order to remove all unbound detection antibody.

Measurement of Bound Detection Antibody.

The amount of detection antibody bound to reference antibody is determined by using the appropriate method for measuring and quantifying the amount of label present. Depending on the label chosen, methods of measuring may include measuring enzymatic activity against added substrate, measuring binding to a detectable binding partner (e.g., for biotin) scintillation counting to measure radioactivity, or any other suitable method to be determined by one of skill in the relevant art.

In the embodiment described above using goat anti-Human IgG Fc HRP polyclonal antibody as the detection antibody, 50 ul of the chromogenic HRP substrate tetramethylbenzidine (TMB) is added to each well. The substrate solution is incubated for about 30 minutes at room temperature. The HRP/TMB reaction is stopped by adding 50 ul of 1M phosphoric acid to each well.

Quantification.

The amount of bound label is then quantified by the appropriate method, such as spectrophotometric measurement of formation of reaction products or binding complexes, or calculation of the amount of radioactive label detected. Under the conditions disclosed here, the amount of label measured in this step is a measure of the amount of labeled detection antibody bound to the reference antibody.

In the embodiment described above using goat anti-Human IgG Fc HRP polyclonal antibody and TMB substrate, the amount of detection antibody bound to reference antibody is quantified by reading the absorbance (optical density or "OD") at 450 nm of each well of the plate.

Data Analysis to Determine Optimal Antigen Concentration.

A known reference antibody concentration is chosen, and the results from wells having the chosen antibody concentration and different amounts of antigen are examined. The antigen concentration that produces the desired signal strength, or standard signal, is chosen as the optimal antigen concentration for subsequent experiments. The standard signal may be empirically determined according to the conditions and materials used in a particular embodiment, because the standard signal will serve as a reference point for comparing signals from other reactions. For a detection method that produces a chromogenic product, a desirable standard signal is one that falls within the most dynamic region of the ELISA reader or other detector and may be an optical density (OD) of between about 0.4 and 1.6 OD units and for this system preferably about 1.0 OD units, although it is possible to achieve signals ranging from 0.2 to greater than 3.0 OD units. Any OD value may be chosen as the standard signal, although an OD value of about 1.0 OD units permits a accurate measurement of a range of test signals above and below 1.0 OD units, and further permits easy comparison with other test signals and reference signals. The concentration of antigen identified as the concentration that produces the standard signal will be used in subsequent experiments to screen and kinetically rank antibodies.

In a preferred embodiment using a 96-well plate, a reference antibody concentration of 100 ng/ml is chosen. It is possible, depending on the sensitivity and antibody concentrations employed in the system, to use other reference antibody concentrations. The signals from the detection antibody reaction in the wells in all columns of the row containing 100 ng/ml antibody are then examined to find the antigen concentration that produces an OD value of about 1.0. In the preferred embodiment described above using goat anti-Human IgG Fc HRP polyclonal antibody and TMB substrate, the wells in the row containing 100 ng/ml antibody are examined to determine which antigen concentration produces a reaction which, when absorbance is measured at 450 nm, has an OD value of about 1.0. This concentration of antigen will then be used for the subsequent experiments to screen and kinetically rank antibodies. A similar approach for identifying optimal antigen densities was used for the Luminex bead based system.

Screening Antibodies Using Limiting Antigen Concentrations

Coat Surfaces at Optimized Antigen Concentration

The surface or surfaces being used to carry out antibody screening are coated with antigen at the optimal concentration as previously determined. In a preferred embodiment, the surfaces are wells of a 96-well streptavidin plate such as a Sigma SA plate, and biotinylated antigen at optimal concentration is added the wells. In a more preferred embodiment, 50 ul of antigen in a solution of 1% skim milk, 1x PBS pH 7.4, and plates are incubated for 30 minutes. In another preferred embodiment, unmodified antigen is added to Costar® Universal-BIND™ plates, and incubation and UV-mediated antigen binding are carried out according to manufacturer's instructions and/or standard protocols, as described above.

After incubation with antigen solution for a suitable amount of time, plates are washed to remove unbound antigen, preferably at least four times (4x).

Addition of Test Antibodies to be Screened and Ranked

Antibodies to be screened and ranked by the limiting antigen assay are called test antibodies. Test antibodies may be recovered from the solution surrounding antibody-producing cells. Preferably, test antibodies are recovered from the media of antibody-producing B cell cultures, hybridoma supernatants, antibody or antibody fragments expressed from any type of cell, more preferably from the supernatant of B cell cultures. Solutions containing test antibodies, for example B cell culture supernatants, generally do not require additional processing; however, additional steps to concentrate, isolate, or purify test antibodies would also be compatible with the disclosed methods.

Each solution containing test antibodies is diluted to bring the concentration within a desirable range and samples are added to a surface having attached antigen. Typically, a desirable concentration range for test antibodies has a maximum concentration lower than the concentration of reference antibody used to select the optimal antigen concentration as described above. One aspect of the present invention provides that a test antibody would produce a signal higher than that of the reference antibody for the same antigen concentration if the test antibody (a) has a higher affinity for the antigen, or (b) has a similar affinity but is present in higher concentration than the reference antigen. Thus, when test antibodies are used at concentrations lower than the concentration of the reference antibody used to select the antigen concentration used in the screening assay, only a test antibody having higher affinity for the antigen would produce a higher signal than the reference antibody signal.

In one embodiment in which a reference antibody concentration of 100 ng/ml is used to select the optimal antigen concentration (as described above), B cell culture supernatants having an empirically determined test antibody concentration range of between about 20 ng/ml to 800 ng/ml are typically diluted ten-fold to produce a working assay test antibody concentration of between about 2 ng/ml to 80 ng/ml. Preferably, at least two duplicate samples of each diluted B cell culture supernatant are tested. Preferably, the diluted B cell culture supernatants are added to wells of a microtiter plate, where the wells are coated with antigen at an optimal concentration previously determined using antigen and a reference antibody.

A positive control should be included as part of the screening, wherein the reference antibody used to optimize the assay by determining optimal antigen concentration is diluted and reacted with the antigen. The positive control provides a set of measurements useful both as an internal control and also to compare with previous optimization results in order to confirm, assure, and demonstrate that results from a screening of test antibodies are comparable with the expected results of the positive control, and are consistent with previous optimization results.

In one embodiment, each B cell culture supernatant to be tested is diluted 1:10 in 1% skim milk/1× PBS pH 7.4/0.05% azide, and 50 ul is added to each of two antigen-coated wells of a 96-well plate, such that 48 different samples are present in each 96-well plate. A positive control comprising a dilution series of the reference antibody is preferably added to wells of about one-half a 96-well plate, to provide confirmation and to demonstrate that results of the screening of test antibodies in B cell culture supernatants run in parallel with the positive control are internally consistent and also consistent with previous optimization results.

Test antibodies are incubated with antigen under suitable conditions. Reference antibodies used as positive controls are incubated in parallel under the same conditions. In one preferred embodiment, plates are wrapped tightly, for example with plastic wrap or paraffin film, and incubated with shaking for 24 hours at room temperature.

Add Detection Antibody to Test Antibodies

Plates are washed to remove unbound test antibodies, preferably about five times (5×) with water. Next, a labeled detection antibody that recognizes and binds to the test antibody is added, and the solution is incubated to permit binding of the detection antibody to the test antibody. Detection antibody is also added to the positive control, to confirm the interaction between the reference antibody and detection antibody. The detection antibody may be polyclonal or monoclonal. The detection antibody may be labeled in any matter that allows detection of antibody bound to the reference antibody. The label may be an enzymatic label such as alkaline phosphatase or horseradish peroxidase (HRP), or a non-enzymatic label such as biotin or digoxygenin, or a radioactive label such as $^{32}P$, $^{3}H$, or $^{14}C$, or fluorescence, or it may be any other label suitable for the assay based on reagents, materials, and detection methods available.

In one embodiment, using human test antibodies, 50 ul of goat anti-Human IgG Fc HRP polyclonal antibody (Pierce Chemical Co, Rockford Ill., catalog number 31416) at a concentration of 0.5 ug/ml in 1% skim milk, 1× PBS pH 7.4 is added to each well of microtiter plates containing test antibodies and reference antibodies (as a positive control). The plate is then incubated for 1 hr at room temperature.

Excess solution containing detection antibody is removed, and plates are washed with water repeatedly, preferably at least five times, in order to remove all unbound detection antibody.

Measurement of Bound Detection Antibody.

The amount of detection antibody bound to test antibody (and bound to reference antibody of the control) is determined by using the appropriate method for measuring and quantifying the amount of label present. Depending on the label chosen, methods of measuring may include measuring enzymatic activity against added substrate, measuring binding to a detectable binding partner (e.g., for biotin) scintillation counting to measure radioactivity, or any other suitable method to be determined by one of skill in the relevant art.

In the method described above, using goat anti-Human IgG Fc HRP polyclonal antibody as the detection antibody, 50 ul of the chromogenic HRP substrate tetramethylbenzidine (TMB) is added to each well. The antibody-substrate solution is incubated for about 30 minutes at room temperature. The HRP/TMB reaction is stopped by adding 50 ul of 1M phosphoric acid to each well.

Quantification.

The amount of bound label is then quantified by the appropriate method, such as the spectrophotometric measurement of formation of reaction products or binding complexes, or calculation of the amount of radioactive label detected. In accordance with one aspect of the present invention, the amount of label provides a measure of the amount of labeled detection antibody bound to the test antibody (or, in the positive control, bound to the reference antibody). In accordance with another aspect of the present invention, the amount of label provides a measure of the amount of test antibody bound to antigen. Thus, detecting and quantifying the amount of label provides a means of measuring the binding of test antibody to the test antigen. By comparing the standard signal with the signal that quantifies the amount of test antibody bound to antigen, it is possible to identify test antibodies with higher affinities by searching for test antibodies which give a higher signal than the reference.

In the method described above using goat anti-Human IgG Fc HRP polyclonal antibody and TMB substrate, the amount of detection antibody bound to test antibody (and reference antibody in the positive control) is quantified by reading the absorbance (optical density, OD) at 450 nm of each well of each plate.

Data Analysis to Identify and Rank Antibodies of Interest.

The results from each test antibody are averaged and the standard range is determined. In a preferred embodiment wherein two samples of each test antibody are assayed using a HRP-labeled detection antibody, OD values at 450 nm are averaged and the standard deviation is calculated. The average OD values of test antibodies are compared against the OD value of the standard signal. Values from the positive control assays are also calculated and examined for reliability of the assay.

Test antibodies are kinetically ranked by considering the average OD value and the range of the OD's between replicates. The average OD value provides a measure of the affinity of the test antibody for the antigen, where affinity is determined by comparison with the standard signal, or the OD value of the reference antibody in the positive control. The range provides a measure of reliability of the assay, where a narrow range indicates that the OD values are likely to be accurate measurements of the amount of test antibody bound to the antigen, and a wide range indicates that the OD values may not be accurate measurements of binding. Acceptable standard deviations are typically OD's of between 5-15% of each other. Test antibodies giving the highest OD values, where the standard deviation of the average value is low, are given the highest kinetic ranking.

In one embodiment, wherein the standard signal is 1.0 OD units, any test antibody with both an average OD of greater than 1.0 OD units, and an acceptably low standard deviation, is considered to have a higher affinity for the antigen than the affinity of the reference antibody.

In another embodiment, Luminex based assays using differentially antigen coated beads were used. In this assay antibodies were ranked based on how they bound antigen at higher then at lower antigen densities.

EXAMPLE 1

Determination of Optimal Antigen Concentration

Antigen Preparation

Parathryoid hormone (PTH) was biotinylated using Pierce EZ-Link Sulpho-NHS biotin according the manufacturer's directions (Pierce EZ-link Sulpho-NHS Biotin, (Pierce Chemical Co., Rockford, Ill., Catalogue number 21217). When the antigen could not be biotinylated, Costar UV plates were substituted. The use of Costar UV plates increased the time of the assay and generally required the use of considerably more antigen.

Checkerboard ELISA

An assay laid out in a "checkerboard" arrangement was carried out as described below to determine optimal coating concentration of the antigen. The assay was performed using streptavidin-coated 96-well plates (Sigma SA mitcrotiter plates, Sigma-Aldrich Chemicals, St Louis Mo., Catalogue number-M5432) as follows.

The parathyroid hormone (PTH) antigen was biotinylated using Pierce EZ-link Sulpho-NHS biotin ((Pierce Chemical Co, Rockford Ill., catalog number 21217) according to manufacturer's instructions. Biotinylated antigen diluted in 1% skim milk/1× PBS pH 7.4 in a series of stepwise dilutions from a beginning concentration of 500 ng/ml to a final concentration of 0.5ng/ml. Diluted biotinylated antigen was distributed horizontally across a 96-well Sigma SA microtiter plate (Sigma Aldrich Chemicals, catalogue M-5432), placing 50 ul of each dilution in wells of each of columns 1 through 11, with replicates in each well of rows A-H under each column. No antigen was added to column 12. The plate was incubated at room temperature for 30 minutes. No blocking step was performed because Sigma SA plates are pre-blocked.

The plate was washed four times with tap water. Plates were washed by hand, or using a microplate washer when available.

An anti-PTH antibody with known affinity was used as a reference antibody. Anti-PTH antibody 15g2 was diluted 1% skim milk/1× PBS pH 7.4/0.05% to final initial dilution of 1 ug/ml was serially diluted 1:2, 7 wells to an ending concentration 15 ng/ml and 50 ul of each dilution was distributed in each well of row A to row G, with replicates in each well of columns 1-12. No antibody was added to row H. Plates containing the antigen and reference antibody were incubated at room temperature for approximately 24 hours.

The plate was wrapped tightly ("air tight") with plastic wrap or paraffin film, and incubated overnight with shaking using a Lab Line Titer Plate Shaker at setting 3.

The plates were washed five times (5×) with water to remove unbound reference antibody. Bound reference antibody was detected by adding fifty microliters (50 ul) of 0.5 ug/ml goat anti-Human IgG Fc HRP polyclonal antibody (Pierce Chemical Co, Rockford Ill., catalog number 31416) in 1% skim milk/1× PBS pH 7.4 to each well and incubating the plate 1 hr at room temperature. (Gt anti-Human Fc HRP-Pierce catalogue number-31416).

The plate was washed at least five times (5×) with water to remove unbound goat anti-Human IgG Fc HRP polyclonal antibody Fifty microliters (50 ul) of the HRP substrate TMB (Kirkegaard & Perry Laboratories, Inc, Gaithersberg, Md.) was added to each well and the plate was incubated for one-half hour at room temperature. The HRP-TMB reaction was stopped by adding 50 ul of 1M phosphoric acid to each well. Optical density (absorbance) at 450 nm was measured for each well of the plate.

Data Analysis

Table 2 shows the results from the reference assay using PTH as the antigen and 15g2 anti-PTH as the reference antibody. OD measurements from the row of samples corresponding to the reference antibody concentration of 100 ng/ml were examined to find the antigen concentration that gives an OD of approximately 1.0. This concentration was determined to be approximately 15 ng/ml PTH. This concentration of antigen was considered the optimal antigen concentration and will be used for the subsequent experiments.

TABLE 2

Optical Density Measurements of Test Antibodies Bound to Various Concentrations of PTH

| Reference antibody concentration (ng/mL) | PTH Contration (ng/mL) | | | | | | | | | | | |
|---|---|---|---|---|---|---|---|---|---|---|---|---|
| | 500.00 | 250.00 | 125.00 | 62.50 | 31.25 | 15.63 | 7.81 | 3.91 | 1.95 | 0.98 | 0.49 | 0.00 |
| 1000 | 3.218 | 3.273 | 3.075 | 3.103 | 2.521 | 1.910 | 1.269 | 0.885 | 0.438 | 0.329 | 0.256 | 0.086 |
| 500 | 3.199 | 3.133 | 3.144 | 3.068 | 2.608 | 1.928 | 1.283 | 0.708 | 0.424 | 0.293 | 0.224 | 0.062 |
| 250 | 3.130 | 3.274 | 3.208 | 2.945 | 2.393 | 1.634 | 3.182 | 0.543 | 0.295 | 0.201 | 0.156 | 0.055 |

TABLE 2-continued

Optical Density Measurements of Test Antibodies Bound to Various Concentrations of PTH

| Reference antibody concentration (ng/mL) | PTH Contration (ng/mL) | | | | | | | | | | | |
|---|---|---|---|---|---|---|---|---|---|---|---|---|
| | 500.00 | 250.00 | 125.00 | 62.50 | 31.25 | 15.63 | 7.81 | 3.91 | 1.95 | 0.98 | 0.49 | 0.00 |
| 125 | 3.190 | 3.194 | 3.177 | 2.733 | 2.116 | 1.251 | 0.863 | 0.444 | 0.489 | 0.178 | 0.147 | 0.067 |
| 62.5 | 3.187 | 3.262 | 2.952 | 2.137 | 1.678 | 0.946 | 0.515 | 0.295 | 0.179 | 0.126 | 0.103 | 0.055 |
| 31.3 | 3.148 | 3.001 | 2.628 | 1.767 | 1.168 | 0.604 | 0.336 | 0.199 | 0.131 | 0.098 | 0.127 | 0.063 |
| 16.6 | 2.998 | 2.792 | 2.099 | 1.245 | 0.736 | 0.371 | 0.189 | 0.127 | 0.093 | 0.073 | 0.070 | 0.056 |
| 0 | 0.114 | 0.121 | 0.089 | 0.088 | 0.069 | 0.068 | 0.054 | 0.052 | 0.054 | 0.057 | 0.058 | 0.063 |

EXAMPLE 2

Limiting Antigen Assay of Test Antibodies

SA microtiter plates were coated with biotinylated antigen PTH at the optimal concentration of 15 ng/ml as determined in Example 1. Fifty microliters (50 ul) of biotinylated antigen at a concentration of 15 ng/ml in 1% skim milk/1× PBS pH 7.4 was added to each well, in a dilution pattern as described in Example 1. The plate was incubated for 30 minutes.

Plates were washed four times (4×) with water, and a B-cell culture supernatant containing test antibodies diluted 1:10 in 1% skim milk/1× PBS pH 7.4/0.05% azide, and 50 ul of each sample was added to each of two wells. Forty-eight (48) different samples were added per 96 well plate. On a separate plate, reference antibody 15g2 anti-PTH at the concentration used to determine the optimal antigen concentration was diluted out at least half a plate. This provided a positive control to assure that results from assays of test antibodies are comparable with optimization results.

Plates were wrapped tightly with plastic wrap or paraffin film, and incubated with shaking for 24 hours at room temperature.

On the following day, all plates were washed five times (5×) and 50 ul goat anti-Human IgG Fc HRP polyclonal antibody at a concentration of 0.5 ug/ml in 1% milk, 1× PBS pH 7.4 was added to each well. The plates were incubated for 1 hour at room temperature.

Plates were washed at least five times (5× with tap water). Fifty microliters (50) ul of HPR substrate TMB was added to each well, and the plate were incubated for 30 minutes. The HRP-TMB reaction was stopped by adding 50 ul of 1M phosphoric acid to each well. Optical density (absorbance) at 450 nm was measured for each well of the plate.

Data Analysis

OD values of test antibodies were averaged and the range was calculated. Antibodies with the highest signal and acceptably low standard deviation were selected as antibodies having a higher affinity for the antigen than did the reference antibody.

Table 3 shows the results of a limiting antigen dilution assay using PTH as a ligand. Antibodies are ranked according to their relative affinity for various PTH antigens, and identified by their well number.

TABLE 3

Affinity Ranking of Test Antibodies to Limited Dilution of PTH

| Well | Limiting Ag OD | Limiting Ag Rank | Primary OD | Secondary OD | PTH(1-84) | PTH(7-84) | PTH(17-44) | Rat PTH(1-84) |
|---|---|---|---|---|---|---|---|---|
| 292A10 | 2.747 | 1 | 0.992 | ND | 1.40 | 1.95 | 3.26 | 0.62 |
| 302A7 | 1.376 | 2 | 0.317 | ND | 0.35 | 0.36 | 2.66 | 0.19 |
| 253D10 | 1.009 | 3 | 0.954 | 0.511 | 0.79 | 1.10 | 2.10 | 1.18 |
| 263C8 | 0.693 | 5 | 0.372 | 0.286 | 1.75 | 1.98 | 3.29 | 1.34 |
| 245B10 | 0.644 | 6 | 0.622 | 0.580 | 0.84 | 0.32 | 0.12 | 0.19 |
| 238F8 | 0.566 | 7 | 0.667 | 0.541 | 1.05 | 1.34 | 2.79 | 1.19 |
| 228E3 | 0.504 | 8 | 0.560 | 0.259 | 0.48 | 0.80 | 3.12 | 1.40 |
| 262H1 | 0.419 | 9 | 0.461 | 0.274 | 0.86 | 1.20 | 2.45 | 0.36 |
| 161G7 | 0.411 | 10 | 0.409 | 0.212 | 0.49 | 0.90 | 1.88 | 0.84 |
| 331H6 | 0.322 | 11 | 0.312 | ND | 0.52 | 0.45 | 2.40 | 0.24 |
| 287E7 | 0.261 | 12 | 0.682 | ND | 0.71 | 0.13 | 0.36 | 1.03 |
| 315D8 | 0.221 | 13 | 0.441 | ND | 0.14 | 0.17 | 0.29 | 0.31 |
| 279E6 | 0.213 | 14 | 0.379 | ND | 0.31 | 0.10 | 0.17 | 0.19 |
| 250G6 | 0.178 | 15 | 0.560 | 0.248 | 0.44 | 0.66 | 1.77 | 0.19 |
| 244H11 | 0.175 | 16 | 0.405 | 0.556 | 0.50 | 0.86 | 0.98 | 0.31 |
| 313D5 | 0.170 | 17 | 0.664 | ND | 0.12 | 0.29 | 0.43 | 0.30 |
| 339F5 | 0.120 | 18 | 0.319 | ND | 0.40 | 0.21 | 0.11 | 0.25 |
| 279D2 | 0.114 | 19 | 0.353 | ND | 0.31 | 0.11 | 0.27 | 0.18 |
| 307H1 | 0.084 | 20 | 0.401 | ND | 0.10 | 0.14 | 0.30 | 0.42 |
| 308A1 | 0.079 | 21 | 0.312 | ND | 0.19 | 0.22 | 0.30 | 0.45 |
| 322F2 | ND | 22 | 1.870 | ND | 1.01 | 0.15 | 0.34 | 1.41 |

EXAMPLE 3

Dilutions of Antibodies Against Interleukin-8 (IL-8)

The proper coating concentration of IL-8 was determined as described above to determine a concentration of IL-8 that resulted in an OD of approximately 1. The optimal concentration was then incubated with a variety of anti-IL-8 antibody supernatants derived from XenoMouse animals immunized with IL-8. Table 4 illustrates typical results and ranking of antibodies screened for their affinity for IL-8. The columns "primary OD" and "secondary OD" refer to primary and secondary binding screen OD's achieved when non-limited amounts of IL-8 were used in the binding ELISA. OD values reported in the limited antigen section refer to an average of two binding ELISA's done at limited antigen. As shown by Table 4, the top three antibodies are able retain their binding to antigen even at the limited concentrations. Other antibodies which also achieved high OD's in the primary and secondary non-limited antigen binding ELISA were not able to achieve the same signal when antigen concentrations were limiting.

TABLE 4

Affinity Ranking of Test Antibodies to Limited Dilution of IL-8

| Clone Number | | Primary | Secondary | Limited Ag | | |
|---|---|---|---|---|---|---|
| plate | well | OD | OD | Average | St dev. | Rank |
| 36 | C6 | 1.95 | 3.023 | 1.32 | 4% | 1 |
| 6 | G11 | 2.021 | 1.403 | 0.90 | 9% | 2 |
| 50 | B1 | 1.818 | 2.398 | 0.82 | 14% | 3 |
| 41 | C11 | 1.83 | 3.218 | 0.81 | 19% | 4 |
| 53 | G5 | 1.128 | 2.521 | 0.80 | 1% | 5 |
| 44 | B8 | 2.09 | 2.707 | 0.78 | 2% | 6 |
| 51 | G10 | 1.408 | 1.652 | 0.78 | 2% | 7 |
| 53 | E1 | 1.992 | 3.035 | 0.72 | 12% | 8 |
| 38 | C1 | 2.571 | 2.945 | 0.71 | 3% | 9 |
| 32 | F3 | 2.339 | 3.322 | 0.66 | 13% | 10 |
| 13 | F10 | 1.505 | 1.833 | 0.66 | 5% | 11 |
| 41 | D2 | 2.997 | 2.944 | 0.66 | 5% | 12 |
| 53 | C2 | 1.56 | 1.869 | 0.64 | 22% | 13 |
| 14 | E2 | 1.255 | 1.875 | 0.57 | 25% | 14 |
| 54 | C3 | 2.131 | 2.486 | 0.51 | 12% | 15 |
| 50 | F3 | 0.572 | 1.635 | 0.51 | 26% | 16 |
| 55 | E8 | 1.031 | 1.917 | 0.50 | 10% | 17 |
| 42 | E5 | 3.07 | 3.147 | 0.49 | 4% | 18 |
| 6 | E7 | 0.637 | 1.545 | 0.49 | 22% | 19 |
| 7 | E10 | 1.794 | 1.953 | 0.48 | 18% | 20 |
| 8 | B2 | 1.725 | 1.777 | 0.48 | 5% | 21 |
| 48 | E6 | 2.103 | 3.004 | 0.48 | 25% | 22 |
| 33 | A1 | 2.623 | 2.351 | 0.47 | 17% | 23 |
| 51 | F5 | 2.062 | 2.838 | 0.45 | 15% | 24 |
| 51 | B1 | 1.778 | 2.631 | 0.45 | 0% | 25 |
| 44 | A5 | 2.473 | 2.55 | 0.44 | 5% | 26 |
| 6 | G4 | 2.117 | 1.SOS | 0.41 | 7% | 27 |
| 43 | G4 | 0.991 | 1.943 | 0.41 | 2% | 28 |
| 47 | E3 | 1.049 | 2.222 | 0.40 | 16% | 29 |
| 46 | F11 | 1.641 | 1.843 | 0.39 | 9% | 30 |
| 43 | F4 | 0.744 | 1.449 | 0.39 | 7% | 31 |
| 54 | H1 | 1.465 | 1.584 | 0.38 | 25% | 32 |
| 44 | F4 | 2.OS | 2.573 | 0.38 | 13% | 33 |
| 49 | G11 | 1.334 | 2.019 | 0.37 | 6% | 34 |
| 11 | C10 | 1.169 | 1.498 | 0.37 | 3% | 35 |
| 41 | B12 | 1.107 | 1.347 | 0.37 | 3% | 36 |
| 46 | F2 | 0.865 | 1.15 | 0.37 | 11% | 37 |
| 52 | E11 | 0.961 | 2.034 | 0.37 | 5% | 38 |
| 7 | B6 | 2.039 | 1.802 | 0.33 | 6% | 39 |
| 39 | F6 | 1.434 | 1.196 | 0.33 | 6% | 40 |
| 10 | E5 | 0.886 | 1.262 | 0.33 | 6% | 41 |
| 36 | C12 | 1.078 | 1.991 | 0.33 | 10% | 42 |
| 44 | B9 | 1.469 | 1.683 | 0.32 | 4% | 43 |

TABLE 4-continued

Affinity Ranking of Test Antibodies to Limited Dilution of IL-8

| Clone Number | | Primary | Secondary | Limited Ag | | |
|---|---|---|---|---|---|---|
| plate | well | OD | OD | Average | St dev. | Rank |
| 8 | H1 | 1.338 | 1.316 | 0.31 | 2% | 44 |
| 52 | F3 | 1.289 | 1.204 | 0.28 | 16% | 45 |
| 45 | A4 | 1.136 | 1.302 | 0.28 | 13% | 46 |
| 25 | A11 | 1.199 | 1.17 | 0.27 | 25% | 47 |
| 51 | C12 | 0.955 | 1.148 | 0.26 | 11% | 48 |
| 6 | E5 | 1.41 | 1.138 | 0.24 | 8% | 49 |
| 39 | H3 | 0.471 | 1.155 | 0.23 | 6% | 50 |
| 14 | E3 | 1.958 | 1.255 | 0.22 | 15% | 51 |
| 3 | D1 | 2.254 | 3.497 | 0.21 | 24% | 52 |
| 33 | F4 | 1.323 | 1.408 | 0.21 | 24% | 53 |
| 51 | A12 | 0.555 | 1.522 | 0.19 | 17% | 54 |
| 5 | G1 | 2.205 | 2.274 | 0.17 | 4% | 55 |
| 35 | C9 | 1.217 | 1.249 | 0.17 | 4% | 56 |
| 6 | B10 | 1.006 | 1.145 | 0.17 | 8% | 57 |
| 39 | B4 | 1.326 | 1.62 | 0.17 | 8% | 58 |
| 5 | G3 | 1.192 | 1.387 | 0.17 | 29% | 59 |
| 35 | F10 | 1.307 | 1.777 | 0.17 | 29% | 60 |
| 17 | E11 | 0.839 | 1.805 | 0.17 | 15% | 61 |
| 3 | D3 | 0.605 | 1.351 | 0.16 | 5% | 62 |
| 31 | A1 | 1.557 | 1.826 | 0.16 | 17% | 63 |
| 28 | C5 | 1.373 | 1.942 | 0.16 | 5% | 64 |
| 14 | F5 | 1.441 | 1.482 | 0.15 | 25% | 65 |
| 43 | D8 | 0.714 | 1.501 | 0.15 | 22% | 66 |
| 29 | D5 | 1.326 | 1.322 | 0.14 | 23% | 67 |
| 32 | F11 | 1.36 | 1.284 | 0.48 | 71% | 68 |
| 7 | D4 | 0.874 | 2.333 | 0.44 | 34% | 69 |
| 47 | G11 | 0.811 | 1.209 | 0.42 | 76% | 70 |
| 39 | G2 | 0.676 | 1.157 | 0.42 | 32% | 71 |
| 15 | G4 | 2.046 | 2.461 | 0.39 | 41% | 72 |
| 31 | G12 | 1.902 | 1.929 | 0.36 | 44% | 73 |
| 41 | C2 | 1.201 | 2.522 | 0.33 | 34% | 74 |
| 7 | E11 | 1.402 | 1.719 | 0.32 | 50% | 75 |
| 40 | A4 | 1.786 | 1.427 | 0.32 | SO% | 76 |
| 45 | E12 | 1.986 | 2.887 | 0.26 | 54% | 77 |
| 2 | B10 | 1.871 | 1.389 | 0.22 | 38% | 78 |
| 7 | H8 | 1.516 | 1.171 | 0.22 | 45% | 79 |
| 28 | C3 | 1.246 | 1.182 | 0.15 | 52% | 80 |

TABLE 4A

Affinity Measurement of Reference Antibody 1

| Reference antibody 1 | | |
|---|---|---|
| Conc. ng/ml | Limited Ag OD | St. Dev. |
| 125.00 | 1.52 | 1% |
| 62.50 | 1.38 | 2% |
| 31.25 | 1.25 | 12% |
| 15.63 | 1.13 | 28% |
| 7.81 | 0.80 | 2% |
| 3.91 | 0.78 | 18% |
| 1.95 | 0.67 | 0% |
| 0.98 | 0.73 | 8% |
| 0.49 | 0.53 | 18% |
| 0.24 | 0.39 | 17% |

TABLE 4B

Affinity Measurement of Reference Antibody 2

Reference antibody 2

| Conc. ng/ml | Limited Ag OD | St. Dev. |
|---|---|---|
| 125.00 | 0.52 | 23% |
| 62.50 | 0.38 | 11% |
| 31.25 | 0.34 | 1% |
| 15.63 | 0.42 | 43% |
| 7.81 | 0.54 | 13% |
| 3.91 | 0.46 | 30% |
| 1.95 | 0.54 | 9% |
| 0.98 | 0.34 | 9% |
| 0.49 | 0.49 | 32% |
| 0.24 | 0.55 | 38% |

EXAMPLE 4

Affinity Ranking

Preparation of Antigens

In order to increase the effective throughput of the antibody affinity ranking process, we labeled different concentrations of an antigen with different colored beads. In this example, beads from the Luminex system were used. As is known, each bead, when activated, emits light of a varying wavelength. When put in a Luminex reader, the identity of each bead can be readily ascertained.

In this example, a different color of strepavidin luminex bead was bound to each of four concentrations of biotinylated antigen (1 ug/ml, 100 ng/ml, 30ng/ml, and 10 ng/ml). Thus, each concentration of the antigen was represented by a different color bead. The four concentrations were the mixed into a single solution containing all four color-bound concentrations.

All of the antibody samples were then diluted to the same concentration (~500 ng/ml) using Luminex quantitation results or a one-point quantitation by Luminex. A serial dilution (1:5) of all of the samples was then performed so a total of four dilution points were obtained, while preferably diluting enough sample for two plates: a quantitation plate and the ranking plate.

Ranking of Antibodies

In order to rank the antibodies, ~2000 of each mixture of luminex bead-antigen samples was loaded into each well of the luminex plate, and then the well was aspirated. Then 50 ul of each antibody sample (24 samples total) was loaded into each well and left overnight while shaking in 4° C. The plates were washed three times (3×) with washing buffer. Detection with a fluorescent anti-human antibody (hIgG-Phycoerythrin (PE) (1:500 dilution)) that bound 50 ul/well was then performed while shaking at room temperature for 20 min. The plates were then washed three times (3×) with washing buffer. The plates were re-suspended in 80 ul blocking buffer. Next, the plates were loaded in the Luminex.

Data Analysis

Because each well held four different concentrations of the same antigen, that could be distinguished based on color, it was possible to rapidly rank binding affinities of the different antibodies. For example, antibodies that had very strong binding affinity for the antigen bound to even the weakest dilution of antibody. This could be measured by analyzing the amount of fluorescent anti-human antibody bound to the colored bead attached to the weakest antigen concentration. Alternatively, antibodies that did not bind strongly might were only detected as binding with the 1 ug/ml and 100 ng/ml antigen concentrations, but not the 30 ng/ml or 100 ng/ml concentrations.

Data analysis was performed using SoftMax Pro for the quantitation data. The Luminex signal of samples tested at several concentrations were compared. The Samples were then ranked accordingly.

EXAMPLE 5

Comparison of Limiting Antigen Output Compared to Absolute Biacore KD Measurements The following kinetic ranking technique was performed by ELISA and compared to formal BiaCore kinetics. Below in Table 5 is a comparison of a typical limited antigen output as compared to absolute Biacore derived KD measurements. In short, 68 antibodies were ranked (relative to each other) using limited antigen ranked. From the 68 antibodies 17 were scaled up to sufficient quantities for formal affinity measurements using BiaCore technology.

TABLE 5

Comparison of Affinity Measurement Based on Limited Dilutions with Biacore Affinity Measurements

| Sample ID | Limited Antigen Ranking | Biacore Affinity (nM) |
|---|---|---|
| A | 1 | 1.9 |
| B | 3 | 1.9 |
| C | 4 | 1.3 |
| D | 5 | 6.9 |
| E | 7 | 3.3 |
| F | 10 | 17.7 |
| G | 11 | 28.9 |
| H | 12 | 3.8 |
| I | 13 | 4.4 |
| J | 23 | 11.2 |
| K | 28 | 57.8 |
| L | 30 | 29.2 |
| M | 34 | 1667 |
| N | 46 | 115.2 |
| O | 47 | 305.1 |
| P | 51 | 1000 |
| Q | 60 | 33.1 |

Data Analysis

As can be seen overall there is a high degree of correlation between high limited antigen rank and the formal $K_D$. In the case of antibodies which do not correlate well, there are a number of reasons why such discrepancies could exist. For example, although antigen is coated on ELISA plates at a low density avidity effects cannot completely be ruled out. In addition, it is possible that, when coating assay material for the limited antigen ranking technique, certain epitopes could be masked or altered. In Biacore analysis, if antigen is flowed over an antibody coated chip, these epitopes on the antigen could be presented in a different conformation and, therefore, seen at a different relative concentration. This could, in turn, could result in a different kinetic ranking between the two methods.

It is also possible that an antibody with lower Biacore derived affinities may give a high limited antigen rank due to a much higher than average concentration of antigen specific antibody being present in the test sample. This could, in turn, lead to an artificially high limited antigen score.

Importantly, the limited antigen kinetics method did allow a rapid determination of relative affinity and it identified the antibodies with the highest formal affinity of the tested antibodies in this panel. Further, as the limited antigen kinetic relative ranking method is easily scalable to interrogate 1000's of antibodies at early stages of antibody generation it offers significant advantage over other technologies which do not offer similar advantages of scale.

We claim:

1. A method of determining the relative binding affinities of antibodies to an antigen, comprising:
   providing a set of serial dilutions of a target antigen comprising a first dilution of said target antigen and a second dilution of said target antigen;
   providing a set of serial dilutions of a reference antibody that binds to said target antigen;
   incubating each dilution of said reference antibody with each dilution of said target antigen;
   measuring the relative degree to which the antibody in each dilution of said reference antibody binds to the target antigen in each dilution of said target antigen;
   selecting the dilution of said target antigen at which differences in the relative degree to which the antibody in each dilution of said reference antibody binds to said target antigen are greater than the differences in the relative degree to which the antibody in each dilution of said reference antibody binds to said target antigen in another dilution of said target antigen, wherein the selected dilution is such that a desired signal strength is produced by the binding of said reference antibody to said target antigen;
   providing a set of test antibody solutions, wherein the concentration of antibody in each test antibody solution is within the concentration range of antibody in said serial dilutions of said reference antibody;
   incubating the selected dilution of said target antigen with each test antibody solution in the set of test antibody solutions;
   measuring the relative degree to which the test antibody in each test antibody solution binds to the target antigen in said selected dilution of said target antigen; and
   ranking the test antibodies in each test antibody solution based on said relative degree to which the test antibodies in each test antibody solution bind to the target antigen in said selected dilution of said target antigen in order to determine the relative binding-affinity of each test antibody to said target antigen.

2. The method of claim 1, wherein the test antibodies are selected from the group consisting of: mammalian, human, humanized, non-human primate, mouse, rat, rabbit, goat, horse, guinea pig, sheep, cow, and chimeric antibodies.

3. The method of claim 1, wherein the test antibodies are recombinant antibodies.

4. The method of claim 1, wherein the test antibodies are antibody fragments.

5. The method of claim 1, wherein measuring the relative degree comprises an assay selected from a group consisting of: an enzyme linked immunosorbent assay (ELISA), a fluorescence-linked immunosorbent assay, a radioisotopic assay (HA), and a surface Plasmon resonance (SPR) based assay.

6. The method of claim 1, wherein the concentration of each test antibody is between 10 ng/ml and 100 ng/ml.

7. The method of claim 1, wherein said concentration of each test antibody is between 10 ng/ml and 50 ng/ml.

8. The method of claim 1, wherein said concentration of each test antibody is between 10 ng/ml and 25 ng/ml.

9. The method of claim 1, wherein said set of test antibody solutions comprises a set of supernatants comprising monoclonal antibodies secreted from a set of hybridomas.

10. The method of claim 1, wherein said set of test antibody solutions is between 100 and 5000 antibody solutions.

11. The method of claim 1, wherein said set of test antibody solutions is between 2500 and 5000 antibody solutions.

12. The method of claim 1, wherein each test antibody solution is a polyclonal antibody solution.

13. The method of claim 1, wherein each test antibody solution is a monoclonal antibody solution.

14. A method of determining the relative binding affinities of a set of molecules to a target molecule binding partner, comprising:
   providing a reference molecule that binds to a target molecule binding partner;
   determining the optimal concentration of the target molecule binding partner for the reference molecule, wherein the optimal concentration is the concentration of said target molecule binding partner at which differences in the relative degree to which the reference molecule binds to said target molecule binding partner are greater than differences in the relative degree to which the reference molecule binds to said target molecule binding partner in another concentration of said target molecule binding partner, and wherein the optimal concentration is such that a desired signal strength is produced by the binding of said reference molecule to said target molecule binding partner;
   providing a set of test molecule solutions, wherein the concentration of molecules in each test molecule solution is within a predetermined concentration of molecules;
   incubating the optimal concentration of the target molecule binding partner with each test molecule solution in the set of test molecule solutions;
   measuring the relative degree to which the test molecules in each test molecule solution bind to the optimal concentration of target molecule binding partner; and
   ranking the test molecules in each test molecule solution based on said relative degree to which the test molecules in each test molecule solution bind to said optimal concentration of target molecule binding partner in order to determine the relative binding affinities of each test molecule to said target molecule binding partner.

15. The method of claim 14, wherein said test molecules are antibodies is an antibody and said target molecule binding partner is an antigen.

16. The method of claim 15, wherein the antibody is selected from the group consisting of: mammalian, human, humanized, non-human primate, mouse, rat, rabbit, goat, horse, guinea pig, sheep, cow, recombinant and chimeric antibodies.

17. The method of claim 15, wherein the antibody is a monoclonal antibody.

18. The method of claim 14, wherein said molecule is a ligand and said target molecule binding partner is a receptor.

19. The method of claim 1, wherein the desired signal strength is an optical density (OD) of between about 0.4 and 1.6 OD units.

20. The method of claim 1, wherein the desired signal strength is an OD of about 1.0 OD units.

* * * * *

UNITED STATES PATENT AND TRADEMARK OFFICE
CERTIFICATE OF CORRECTION

PATENT NO. : 7,754,433 B2  
APPLICATION NO. : 10/309421  
DATED : July 13, 2010  
INVENTOR(S) : John Babcock et al.

Page 1 of 1

It is certified that error appears in the above-identified patent and that said Letters Patent is hereby corrected as shown below:

Col. 15-16, line 10 (Approx. Table 2)     Change "16.6" to --15.6--

Col. 17, line 53 (Approx. Table 4)        Change "1.SOS" to --1.505--

Col. 17, line 58 (Approx. Table 4)        Change "2.0S" to --2.05--

Col. 18, line 44 (Approx. Table 4)        Change "SO%" to --50%--

Col. 21, line 61        "(HA)" should read --(RIA)--.

Col. 22, line 49        Delete "is an antibody".

Signed and Sealed this  
First Day of February, 2011

David J. Kappos  
*Director of the United States Patent and Trademark Office*